(12) United States Patent  
Kishida et al.

(10) Patent No.: US 8,801,179 B2  
(45) Date of Patent: Aug. 12, 2014

(54) OPHTHALMOLOGIC PHOTOGRAPHING APPARATUS

(75) Inventors: Nobuyoshi Kishida, Musashino (JP); Shinya Tanaka, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 224 days.

(21) Appl. No.: 12/712,098

(22) Filed: Feb. 24, 2010

(65) Prior Publication Data

US 2010/0214536 A1    Aug. 26, 2010

(30) Foreign Application Priority Data

Feb. 26, 2009 (JP) .................................. 2009-043990

(51) Int. Cl.
- *A61B 3/14* (2006.01)
- *A61B 3/12* (2006.01)
- *A61B 3/00* (2006.01)

(52) U.S. Cl.  
CPC ............. *A61B 3/1241* (2013.01); *A61B 3/0058* (2013.01); *A61B 3/0041* (2013.01)  
USPC ......................................... 351/206; 351/246

(58) Field of Classification Search  
CPC ...... A61B 3/0041; A61B 3/0058; A61B 3/12; A61B 3/1233; A61B 3/1241  
USPC ................................................ 351/206, 246  
See application file for complete search history.

(56) References Cited

U.S. PATENT DOCUMENTS 7,147,328 B2 * 12/2006 Sugino et al. ................. 351/206

FOREIGN PATENT DOCUMENTS

| JP | 2001-245851 A | 9/2001 | |
|---|---|---|---|
| JP | 2003-010129 A | 1/2003 | |
| JP | 2004-187811 A | 7/2004 | |
| JP | 2005-006926 A | 1/2005 | |
| JP | 2005006894 A * | 1/2005 | ............... A61B 3/14 |

OTHER PUBLICATIONS

Machine Translation of JP 2005-006894.*  
Certified Translation of JP 2005-006894.*

* cited by examiner

*Primary Examiner* — Zachary Wilkes  
(74) *Attorney, Agent, or Firm* — Canon U.S.A., Inc., IP Division

(57) ABSTRACT

An ophthalmologic photographing apparatus includes a photographing mode selection unit configured to select one of a plurality of photographing modes respectively corresponding to different photographing conditions, an imaging unit configured to capture an image of a subject's eye, an original image data generation unit configured to process electronic data of the image captured by the imaging unit according to the selected photographing mode and to generate a plurality of original image data differing from one another in spatial resolution and gradation resolution, and an image processing unit configured to generate a electronic image for diagnosis, which has similar gradation resolution to that of each of the plurality of original image data generated by the original image data generation unit.

34 Claims, 5 Drawing Sheets

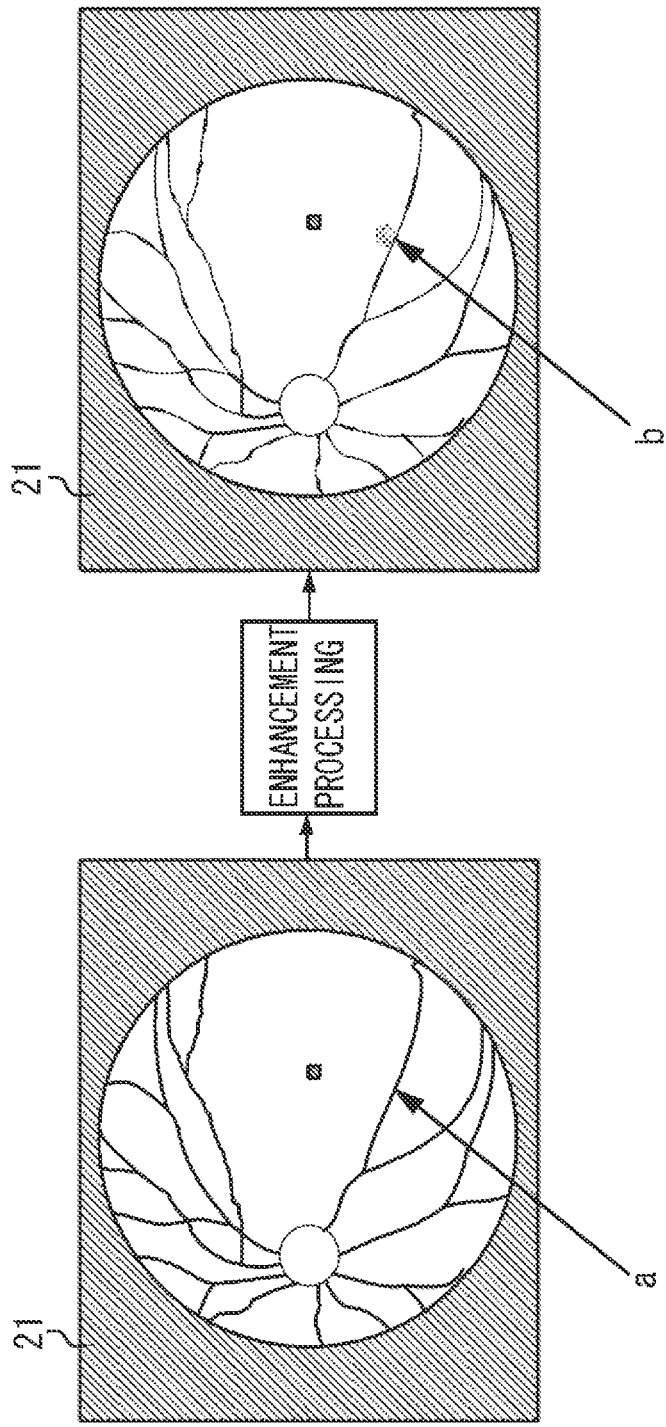

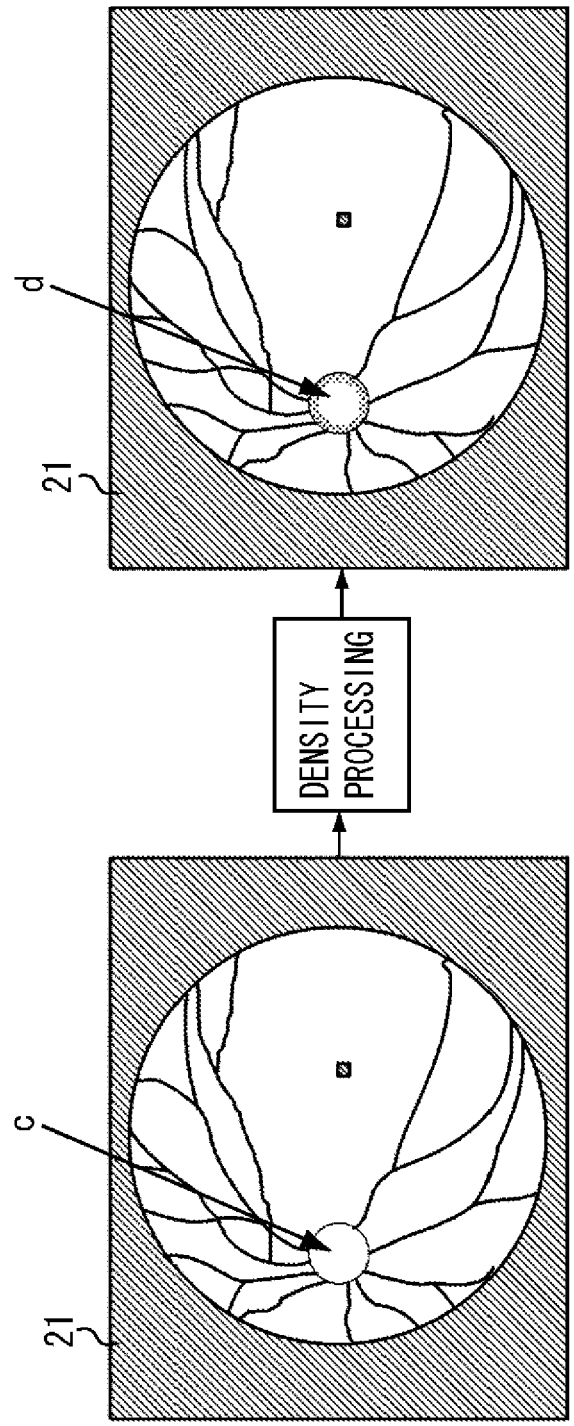

OPHTHALMOLOGIC PHOTOGRAPHING APPARATUS

BACKGROUND OF THE INVENTION

1. Field of the Invention

The present invention relates to an ophthalmologic photographing apparatus used in an ophthalmologic doctor's office, a group medical examination, or the like for photographing a subject's eye and performing image processing on a photographed fundus image.

2. Description of the Related Art

A fundus camera for photographing a fundus of a subject's eye has been known as an ophthalmologic photographing apparatus. Particularly, a fundus camera has been known, which has a plurality of photographing modes, such as a color photographing mode, a visible fluorescent photographing mode (fluorescent angiography (FAG) photographing mode) and an infrared fluorescent photographing mode (indocyanin green (ICG) photographing mode), in order to observe a subject's eye and to perform photographing according to an examination purpose.

Japanese Patent Laid-Open No. 2001-245851 discusses an apparatus that automatically sets parameters, such as again, a gamma value, or a color temperature, for a television camera mounted in an ophthalmologic photographing apparatus according to the plurality of photographing modes. Japanese Patent Laid-Open No. 2004-187811 discusses an apparatus that performs image processing with an optimum processing parameter corresponding to each of the plurality of photographing modes.

When visible fluorescent photographing of a fundus of a subject's eye is performed, an original image obtained by the visible fluorescent photographing is a greenish color image. However, for easier image-interpretation, the color image is converted into a monochrome image. In addition, gradation conversion processing, such as gamma characteristic adjustment or contrast processing, is performed as the image processing using the above optimum processing parameters. Similarly, when infrared fluorescent photographing of a fundus of a subject's eye is performed, generally, diagnosis is made using an image that is obtained by performing gamma characteristic adjustment, contrast processing, or the like.

Conventional ophthalmologic photographing apparatuses having a plurality of photographing modes have employed the following two methods.

(1) A method of performing, just after an image of a subject's eye is photographed, image processing on a raw captured image of the subject's eye and then conducting image-interpretation of a compressed image.

(2) A method of storing the entire original captured image of a subject's eye and then performing image-interpretation of the stored original image.

However, when image-interpretation is performed using the method (1), hue information, and gradation information representing density levels or the like are insufficient. Thus, it is difficult to observe a lesion. There is a risk that oversight of a lesion may occur at worst. On the other hand, when image-interpretation is performed by the method (2), gradation information is not insufficient. However, due to a recent high increase in resolution of image sensors, an amount of image data representing a photographed image of a subject's eye has become enormous, with result of reduction in processing speed of ophthalmologic photographing apparatuses and increase in recorded data. Accordingly, loads of ophthalmologic photographing apparatuses increase. Thus, usability thereof becomes poor.

SUMMARY OF THE INVENTION

The present invention is directed to an ophthalmologic photographing apparatus capable of solving the above problems and enhancing accuracy of image-interpretation, without impairing usability.

According to an aspect of the present invention, an ophthalmologic photographing apparatus includes a photographing mode selection unit configured to select one of a plurality of photographing modes respectively corresponding to different photographing conditions, an imaging unit configured to capture an image of a subject's eye, an original image data generation unit configured to process electronic data of the image captured by the imaging unit according to the selected photographing mode and to generate a plurality of original image data differing from one another in spatial resolution and gradation resolution, and an image processing unit configured to generate a electronic image for diagnosis, which has similar gradation resolution to that of each of the plurality of original image data generated by the original image data generation unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 3A and 3B illustrate an example of an image-interpretation for a diabetic retinopathy.

FIGS. 4A and 4B illustrate an example of an image-interpretation for glaucoma diagnosis.

DETAILED DESCRIPTION OF THE EMBODIMENTS

The accompanying drawings, which are incorporated in and constitute a part of the specification, illustrate exemplary embodiments, features, and aspects of the invention and, together with the description, serve to explain the principles of the invention.

Figure 1:
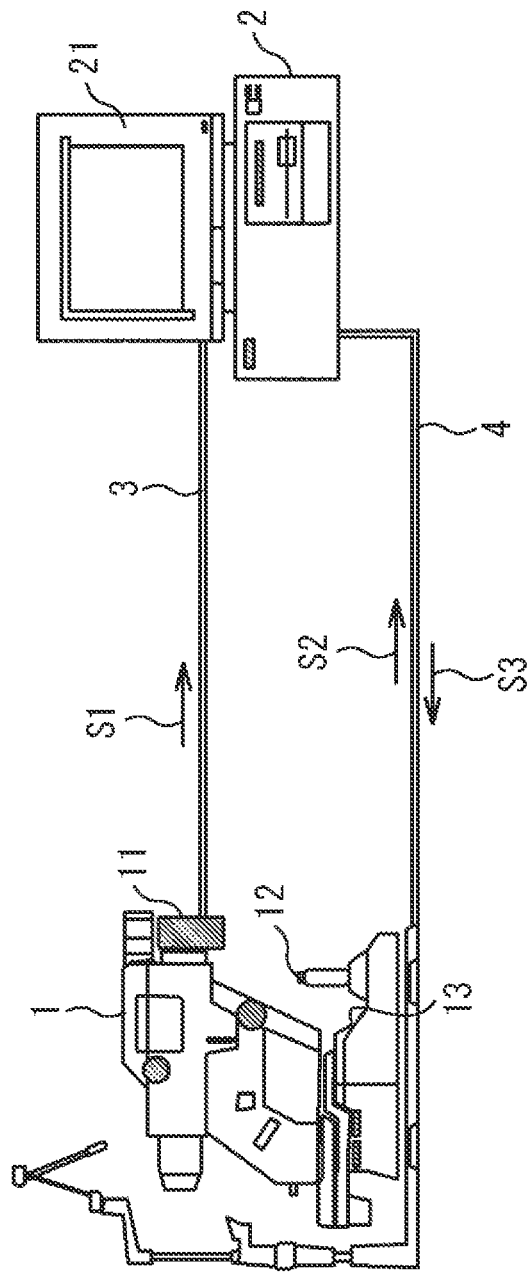
FIG. 1 illustrates a configuration of an ophthalmologic photographing apparatus according to an exemplary embodiment of the present invention.

FIG. 1 illustrates a configuration of an ophthalmologic photographing apparatus having a fundus camera according to an exemplary embodiment of the present invention. The ophthalmologic photographing apparatus includes the fundus camera 1, and a personal computer 2 for image processing and file management. The fundus camera 1 includes a digital camera 11, a photographing start unit 12, and a photographing mode selection unit 13. The digital camera 11 incorporates an imaging unit such as a charge-coupled device (CCD), and generates digital original image data. The photographing start unit 12 includes a switch. Similarly, the photographing mode selection unit 13 includes a switch.

The personal computer 2 includes an image display unit 21 such as a monitor. The fundus camera 1 includes members such as an illumination optical system for illuminating a subject's eye, a photographing optical system, a filter corresponding to each photographing mode, an observation light source, and a photographing light source, though they are not illustrated.

Two communication paths 3 and 4 are used between the fundus camera 1 and the personal computer 2. The communication path 3 is used for data transmission. Original image data S1 is output from the digital camera 1. Photographing information S2 is output from the fundus camera 1 using the communication path 4. The personal computer 2 outputs a photographing enable signal indicating that the ophthalmologic photographing apparatus is put into a state in which a photographing operation is enabled.

Figure 2:
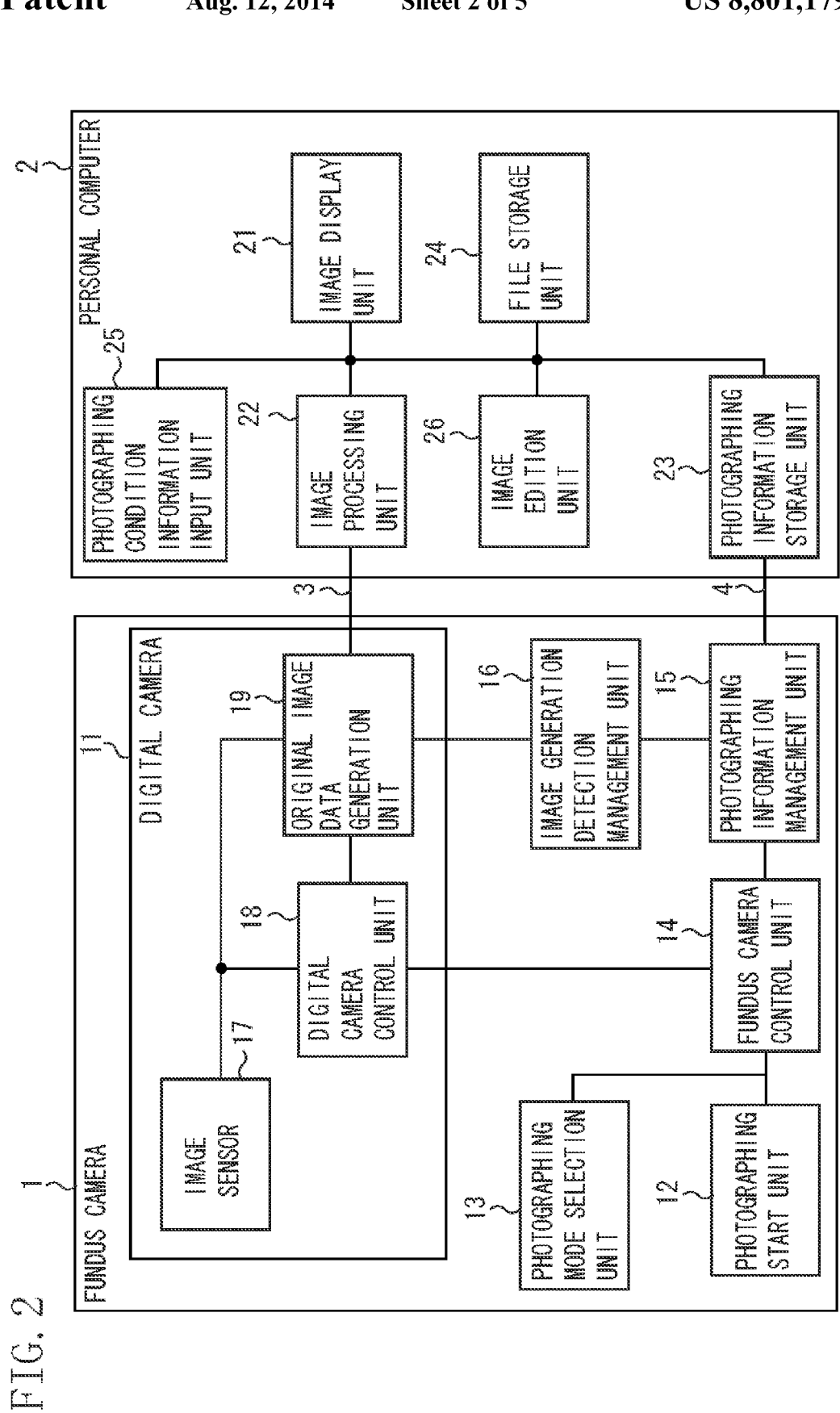
FIG. 2 illustrates a block circuit configuration of the ophthalmologic photographing apparatus according to the exemplary embodiment of the present invention.

FIG. 2 illustrates a block circuit configuration of the ophthalmologic photographing apparatus according to the exemplary embodiment of the present invention. The fundus camera 1 includes a fundus camera control unit 14, a photographing information management unit 15, and an image generation detection management unit 16, in addition to the digital camera 11, the photographing start unit 12, and the photographing mode selection unit 13 described above. The fundus camera control unit 14 controls the fundus camera 1. The image generation detection management unit 16 detects that original image data is generated by the digital camera 11.

In addition, an image sensor 17, such as a CCD, a digital camera control unit 18 for controlling the digital camera 11, and an original image data generation unit 19 for generating original image data to be output by the digital camera 11 are provided in the digital camera 11.

An image processing unit 22, a photographing information storage unit 23, a file storage unit 24, a photographing condition information input unit 25, and an image edition unit 26 are additionally provided in the personal computer (PC) 2. The image processing unit 22 performs image processing, mainly gradation processing, on original image data output from the original image data generation unit 19. The photographing information storage unit 23 stores photographing information output from the photographing information management unit 15 of the fundus camera 1 in the file storage unit. The file storage unit 24 stores image files with photographing information. The photographing condition information input unit 25 inputs photographing condition information such as a patient's name and a photographing location.

The original image data generation unit 19 is provided integrally with a general digital camera. The PC 2 is utilized as the image processing unit 22. The apparatus is configured by connecting the original image data generation unit 19 and the image processing unit 22 to each other with a data transfer unit. Consequently, a simpler and inexpensive system can be provided. In addition, a photographed image can quickly be displayed without unnecessarily increasing a data transfer time at that time.

When a patient to be photographed is determined, the personal computer 2 selects the patient and checks patient information using the photographing condition information input unit 25. Next, in order to enable photographing when the information concerning the patient is definitely determined, the personal computer 2 outputs a photographing enable signal S3 to the fundus camera 1 via the communication path 4. An operation of the fundus camera 1 becomes possible in response to the output of the photographing enable signal S3.

In this state, one of photographing modes is selected using the photographing mode selection unit 13. According to the present exemplary embodiment, a color photographing mode and a fluorescent photographing mode (particularly, a visible fluorescent angiography photographing mode) are employed as the photographing modes. After one of the photographing modes is selected, an alignment operation and a focusing operation are performed on a subject's eye.

When a region to be photographed is determined, an operator photographs an image of a fundus of a subject's eye by operating the photographing start unit 12 of the fundus camera 1. In response to an input from the photographing start unit 12, the fundus camera 1 controls the photographing light source to emit light in synchronization with a photographing synchronization signal output from the digital camera 11.

First, when the color photographing mode is selected, the operator selects the color photographing mode by operating the photographing mode selection unit 13. In response to this operation, the fundus camera control unit 14 changes a currently used filter to a filter for color photographing. When an image of a fundus of a subject's eye is captured, the original image data generation unit 19 of the digital camera 11 performs processing, such as a pixel addition, to reduce a spatial resolution of a captured raw image while a gradation resolution of the raw image is maintained at, e.g., 12 bits multiplied by 3 components (red, green, and blue (RGB)). If necessary, original image data S1 is generated by losslessly compressing raw image data.

Then, the original image data S1 is transferred to the image processing unit 22 of the personal computer 2 through the communication path 3. The transferred original image data S1 is subjected to gradation conversion processing. Finally, a color diagnosis image having a gradation resolution (generally, e.g., 8 bits multiplied by 3 components (RGB)) suitable for being displayed on the image display unit 21 is generated. Then, the color diagnosis image is displayed on the image display unit 21. This image processing process is hereinafter referred to as a "first process".

Subsequently, the color diagnosis image is associated with the original image data S1 and photographing relevant information that is related to the photographing condition information input unit 25 and the photographing information storage unit 23. Then, the image is stored in the file storage unit 24. More specifically, a file stored in the file storage unit 24 includes both of color diagnosis image data and original image data S1 having gradation information of 12-bit gradation information of a raw image.

In other words, photographing control in the color photographing mode is featured in that the original image data generation unit 19 compresses spatial information of a raw image while gradation information of the raw image is maintained. In color photographing, a spatial frequency bandwidth of a photographed image is narrow due to chromatic aberration of a photographing optical system, as compared with that of an image photographed in monochromatic photographing, e.g., fluorescent photographing or red-free photographing, performed by filter photographing using illumination light of a narrower frequency band.

In a color photographing mode in which a color diagnosis image of a narrow spatial frequency band is obtained, original image data is generated by taking precedence of a gradation resolution over a spatial resolution, as compared with a monochromatic photographing mode in which filter photographing, e.g., fluorescent photographing or red-free photographing, is performed using illumination light of a narrower frequency band.

Consequently, redundant space data can appropriately be compressed. Original image data maintaining a higher gradation resolution can be processed by performing image processing at a subsequent stage. Accordingly, appropriate gradation processing can be performed on a gradation expression of a wide dynamic range image of an optic disc and a macula flava on a fundus.

FIG. 3A illustrates a practical example of image processing performed in an image-interpretation process, i.e., a process of interpreting an image of diabetic retinopathy in a color photographing mode. Particularly, FIG. 3A illustrates an image output to the image display unit 21 by performing the first process on a fundus image photographed in color. Because differences in luminance and lightness between a blood vessel and a boundary area thereof are large, the blood vessel can easily be distinguished from the boundary area.

However, when interpretation of a small bleed spot on a region "a" is performed, processing to enhance the differences in luminance and lightness between a target region and a boundary area is effective. Enhancement processing is performed by the image edition unit 26 using an original image data file stored in the file storage unit 24.

An image illustrated in FIG. 3B is obtained by performing enhancement processing on the image illustrated in FIG. 3A. Thus, a region "b" can be interpreted as a small bleed spot by image-interpretation. According to the present embodiment, an original image data file records gradation information of a raw image as it is. Accordingly, interpretation of such a detailed region can be achieved.

FIGS. 4A and 4B illustrate an example of image-interpretation of glaucoma diagnosis. Similar to FIG. 3A, FIG. 4A illustrates an image output to the image display unit 21 by performing the first process. However, a condition of a cribriform plate of an optic disc "c", which is necessary for perceiving a defect of a retinal optic nerve bundle, cannot be grasped due to an insufficient gradation resolution and an inadequate dynamic range of display elements.

However, gradation conversion processing is performed on the original image, whose gradation resolution is maintained, by the image edition unit 26 so that the cribriform plate of the optic disc "d" can be expressed with a large gradation. Consequently, a gradation expression of a wide dynamic range image of the optic disc "d" can be achieved, as illustrated in FIG. 4B. Thus, when a color image is photographed, the gradation information of the raw image is recorded as it is. Accordingly, a diagnosis on a detailed region can be achieved by performing image edition processing on the hue and the gradation of the image.

Other examples of the image processing include enhancement processing and noise removal processing to be performed on a fundus image captured by insufficient exposure, and an image of the fundus of a cataractic eye, which is low in luminance and lightness and contains many dark areas, and useful image edition processing, such as color correction processing, to be performed on a fundus image which does not have natural hue due to differences among fundus pigments.

In a fluorescent photographing mode as an example of a monochrome image, an operator selects a fluorescent photographing mode using the photographing mode selection unit 13. In response to this operation, the fundus camera control unit 14 controls a filter to be changed for fluorescent photographing.

When an image is photographed, the original image data generation unit 19 performs a color decrease process and gradation conversion according to the fluorescent photographing mode. More specifically, the original image data generation unit 19 performs a color decrease process of reducing the gradation resolution of the image from, e.g., 12 bits multiplied by 3 components (RGB) to 8 bits (corresponding to a monochrome image) while the spatial resolution thereof is maintained at a total number of pixels, which is 10 megapixels (M pixels).

If necessary, original image data S1 subjected to lossy compression, e.g., Joint Photographic Experts Group (JPEG) compression is generated. Then, the original image data S1 captured by the digital camera 11 is transferred to the image processing unit 22 of the personal computer 2 through the communication path 3. If necessary, a file of the image data transferred to the image processing unit 22 is restored.

The gradation resolution of the restored image data is already reduced to a value suitable for the image display unit 21, e.g., 8 bits (corresponding to a monochrome image). In addition, appropriate gradation processing is performed on the restored image data. Thus, the restored image is displayed on the image display unit 21 as a display diagnostic image. Then, the image is stored in the file storage unit 24, together with photographing relevant information associating the photographing condition information input unit 25 and the photographing information storage unit 23.

When monochromatic photographing is performed by filter photographing using illumination light with a narrower frequency band, as compared with the frequency band of the illumination light used in the case of performing the above color photographing, original image data is generated by taking precedence of a spatial resolution according to the expanded spatial frequency band over a gradation resolution. Thus, the data can appropriately be compressed. This compression is very effective in performing high-speed continuous shooting in a fluorescent photographing mode.

In the fluorescent photographing mode, an object of the fluorescent photographing is to perform angiography using a fluorescent agent. Thus, most of the entire photographed fluorescent image is taken up by a high-contrast fine blood vessel image part due to a fluorescent agent. Consequently, a spatial resolution corresponding to the spatial frequency band of a wide-band image is required.

On the other hand, the contrast of the blood vessel image is sufficiently high. Sufficient gradation expression of a fundus image can be implemented by the gradation conversion uniquely performed by the original image data generation unit 19. In addition, for easy image-interpretation, the conversion of a color image into a monochrome image is also performed.

In other words, in the fluorescent photographing mode, original image data is generated by performing a "second process" to take precedence of a spatial resolution over a gradation resolution. Thus, the data can appropriately be compressed. For a similar reason, generally, the image processing unit 22 does not need to perform special gradation conversion. Apparently, appropriate gradation processing can be performed again according to special conditions, such as a user's preference, an amount and a type of a fluorescent agent, and an operator's preference.

Figure 5A:
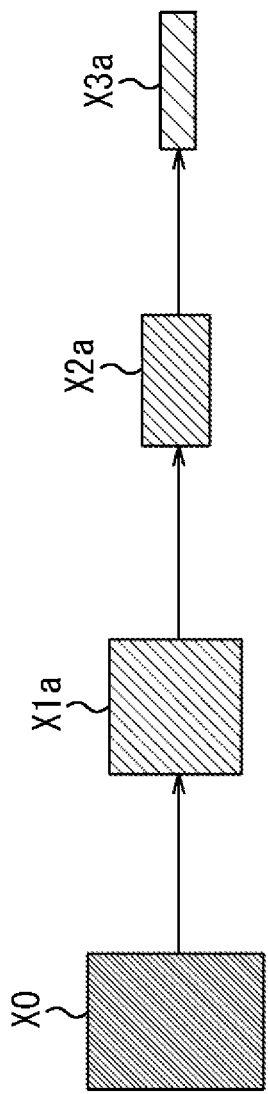
FIGS. 5A, 5B, and 5C illustrate image data processed in the exemplary embodiment of the present invention and a conventional apparatus.

FIG. 5A illustrates image data processed by the "first process" according to the present exemplary embodiment. A size of each block illustrated in FIG. 5A indicates data capacity. Image data X0 is raw image data, i.e., electronic data, before subjected to any process, captured by the image sensor 17.

Image data X1$a$ is original image data generated by the original image data generation unit 19 of the digital camera 11 when color photographing of a fundus image is performed. More specifically, the original image data generation unit 19 of the digital camera 11 performs processing, such as pixel addition, to reduce a spatial resolution of a captured raw image data X0 while a gradation resolution of the raw image data is maintained at, e.g., 12 bits multiplied by 3 components (RGB). If necessary, the raw image data X0 is further subjected to lossless compression. Accordingly, a data amount of image data X1a is less than that of the image data X0.

The image data X1a output by the digital camera 11 is transferred to the image processing unit 22 of the personal computer 2 through the communication path 3. In a case where a communication speed is constant, a communication time is dominated by the data capacity of the image data X1a. Response and usability of the apparatus depend upon the data capacity of the image data X1a. Thus, it is important to optimize this data capacity.

An image X2a is subjected to gradation conversion according to each photographing mode. Finally, the image X2a has a gradation resolution, e.g., 8 bits multiplied by 3 components suitable for the image display unit 21 such as a monitor, which is generally an electronic color image to be used for diagnosis.

After lossy compression such as JPEG is performed, the image X2a is changed to an image X3a to be stored in the file storage unit 24 together with photographing relevant information. However, a data amount of the photographing relevant information is extremely small, as compared with that of the image data. Thus, the data capacity of the image data X3a is further reduced, as compared with reduction in the data capacity of the image data X2a, by the capacity compression using the lossy compression.

Figure 5B:
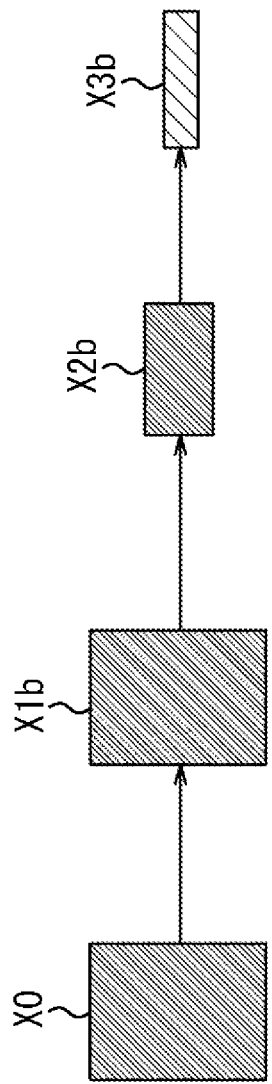

On the other hand, FIG. 5B illustrates a method of recording the gradation information of the raw image as it is by a conventional apparatus. Both of gradation information and spatial information of original image data X1b generated by the original image data generation unit 19 of the digital camera 11 are the same as those of the raw image data, respectively.

Accordingly, the image data X1b is equal in data amount to the image data X0. Image data X2b is electronic image data to be used for diagnosis, which is subjected to the gradation conversion according to each photographing mode and finally has a predetermined gradation resolution suitable for the image display unit 21, generally, e.g., 8 bits multiplied by 3 (RGB). Subsequently, similar to the image X2a illustrated in FIG. 5A, the image X2b is changed to an image X3b to be stored in the file storage unit 24 together with the photographing relevant information.

However, such an apparatus is requested to handle a large amount of data such as the image data X1b when the image data is transferred or when image processing is performed thereon. Thus, a system load is generated, so that the usability of the apparatus is poor.

Figure 5C:
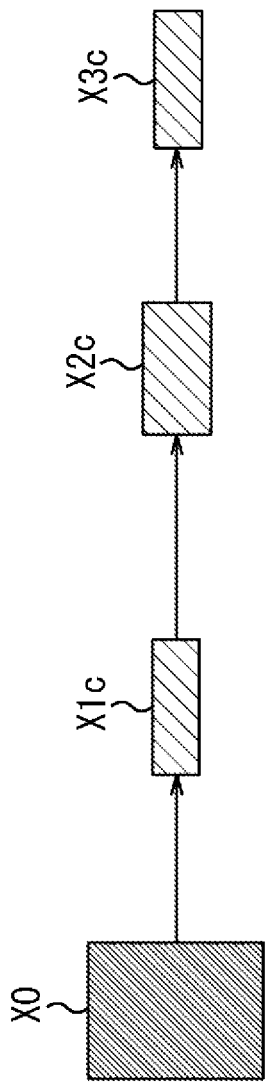

FIG. 5C illustrates conversion of image data in a fluorescent photographing mode by performing the "second process" according to the present exemplary embodiment. Similar to FIGS. 5A and 5B, a size of each block illustrated in FIG. 5C indicates data capacity. As described in the description of the fluorescent photographing mode, a color decrease process and a gradation conversion are performed according to the fluorescent photographing mode.

The original image data generation unit 19 of the digital camera 11 reduces the gradation resolution of the captured raw image X0 from, e.g., a value obtained by 12 bits multiplied by 3 components (RGB) to 8 bits (corresponding to a monochrome image) while the spatial resolution thereof is maintained at a total number of pixels, which is 10 M pixels.

In a case where, if necessary, original image data X1c subjected to lossy compression, e.g., JPEG compression is generated, a file of the original image data X1c transferred to the image processing unit 22 is restored. Thus, the restored image data X2c is obtained.

However, the gradation resolution of the restored image data X2c is already reduced to a value suitable for the image display unit 21, e.g., 8 bits (corresponding to a monochrome image). In addition, appropriate gradation processing is performed on the restored image data X2c. Thus, the restored image can be displayed on the image display unit 21 as an electronic image for diagnostic.

Then, the image X2c is subjected again to the file compression, and stored together with the photographing relevant information associating the photographing condition information input unit 25 and the photographing information storage unit 23 in the file storage unit 24 as a file X3c. Accordingly, as described above, generally, the image processing unit 22 does not need to perform a special gradation conversion.

When high-speed continuous photographing, such as fluorescent photographing, is performed, the system load largely depends on a data amount of data on which image processing is performed. Because the capacity of the image data X1c is less than that of the image data X1b, the system load in the fluorescent photographing mode can be made small, in comparison with that in the color photographing mode. Image data communication and image display, which meet the speed required in the fluorescent photographing mode, can be performed.

However, when this process is employed in the color photographing mode by the conventional apparatus, the image edition unit 26 performs the color decrease process to reduce the gradation resolution of the raw image X0 already captured by the original image data generation unit 19 of the digital camera 11.

Then, processes such as a gamma correction and a contrast correction are performed on the obtained image X2a. Results of the processes are repeatedly output to the image display unit 21. Accordingly, in the color image processing performed in this stage, a sufficient gradation resolution is not maintained. Thus, a desired result cannot be obtained.

To summarize the foregoing description, the system configured to perform the "first process" illustrated in FIG. 5A and employed in the color photographing mode can solve the drawbacks of the conventional apparatus, which are illustrated in FIG. 5B, by taking advantages of a color fundus image, without impairing image quality, and can generate image data that can reduce the system load.

For the color image that needs higher gradation resolution, the system configured to perform the "first process" illustrated in FIG. 5A can analyze original image data input to the image processing unit and can perform processing based on a result, i.e., what is called adaptive processing.

In the first exemplary embodiment of the present invention, an example has been described, in which the image processing unit 22 is manually operated when image-interpretation is performed. However, the image processing unit 22 can perform automatic processing by analyzing the data file corresponding to the original image and by then generating an optimum processing parameters for the original image. In addition, the apparatus can be modified so that a method for generating a plurality of parameters for each region to be subjected to enhancement processing or for each target lesion is prepared, and that an operator can select the parameter according to a requirement.

In a fluorescent photographing mode for obtaining fluorescent diagnosis images, which needs high-speed continuous shooting, the high-speed shooting is enabled by feeding to the data transfer unit image data subjected to lossy compression. When lower-speed shooting is performed, degradation of the image quality generated due to compression can be suppressed by using lossless compression or not using compression. Thus, a precise image for diagnosis can be obtained.

In the first exemplary embodiment of the present invention described above, the fundus camera having two photographing modes, i.e., a color photographing mode and a fluorescent photographing mode has been described by way of example. A fundus camera according to a second exemplary embodiment of the present invention has a plurality of photographing modes including an intermediate photographing mode, such as a red-free photographing mode, which has an intermediate characteristic between the color photographing mode and the fluorescent photographing mode.

For example, in a case of a red-free image photographed in a red-free photographing mode, when a necessary spatial resolution Sr is compared with a spatial resolution Sc needed for a color image, and a spatial resolution Sf needed for a fluorescent image, the spatial resolutions satisfy the following condition: Sc<Sr<Sf. Similarly, a gradation resolution Dr needed for a red-free image, a gradation resolution Dc needed for a color image, and a gradation resolution Df needed for a fluorescent image satisfy the following condition: Dc>Dr>Df.

Accordingly, processing to be performed on a captured raw image by the original image data generation unit 19 of the digital camera 11 is to slightly reduced in the gradation resolution of the raw image to, e.g., 10 bits (corresponding to a monochrome image). It is sufficient that the apparatus is set to perform the "second process" to generate original image data having a spatial resolution higher than the spatial resolution of a color image.

The load can be adjusted, while an image appropriate for the characteristic of each photographing mode is obtained, by appropriately setting such a "second process" according to each photographing mode.

In the first exemplary embodiment of the present invention, an example has been described, in which the gradation resolution is set in the fluorescent photographing mode to be the gradation resolution of a final image used for display and diagnosis, and after this image is transferred to the image processing unit 22, gradation processing is not performed. However, gradation drawing capability can be enhanced by setting the gradation resolution at a little higher value.

It is useful to set the apparatus so that a user can select a plurality of combinations of resolutions for the same photographing mode.

Apparently, selection of a type of a file compression process and an amount of application of the file compression process, which is prepared if necessary, as a parameter can be performed as the processing to be performed by the original image data generation unit 19 on a captured raw image.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-043990 filed Feb. 26, 2009, which is hereby incorporated by reference herein in its entirety.

What is claimed is:

1. An ophthalmologic photographing apparatus comprising:
   a photographing mode selection unit configured to select one of a plurality of photographing modes corresponding to different photographing conditions;
   an imaging unit configured to capture an image of a subject's eye;
   an image data generation unit configured to generate image data having a higher gradation resolution and a lower spatial resolution from electric data of the captured image in a case where a color photographing mode is selected by the photographing mode selection unit than in a case where a fluorescent photographing mode is selected by the photographing mode selection unit.

2. The ophthalmologic photographing apparatus according to claim 1, wherein the image data generation unit performs, in the case where a color photographing mode is selected by the photographing mode selection unit, processing to reduce spatial resolution of the electric data, and
   wherein the image data generation unit performs, in a case wherein the fluorescent photographing mode is selected by the photographing mode selection unit, processing to reduce gradation resolution of the electric data.

3. The ophthalmologic photographing apparatus according to claim 2, further comprising a data transfer unit configured to transfer to the image processing unit the image data generated by the image data generation unit.

4. The ophthalmologic photographing apparatus according to claim 3,
   wherein in a case where a color photographing mode is selected by the photographing mode selection unit, the image data to be transferred is image data subjected to lossless compression, and
   wherein in a case where a fluorescent photographing mode is selected by the photographing mode selection unit, the image data to be transferred is image data subjected to lossy compression.

5. The ophthalmologic photographing apparatus according to claim 1, wherein the image data generation unit generates, in a case wherein the color photographing mode is selected by the photographing mode selection unit, an image data whose gradation resolution of the electric data is maintained, and wherein the image data generation unit generates, in a case where the fluorescent photographing mode is selected by the photographing mode selection unit, image data whose spatial resolution of the electric data is maintained.

6. The ophthalmologic photographing apparatus according to claim 1, further comprising an image processing unit configured to generate an electronic image for diagnosis, which has similar gradation resolution to that of the generated image data,
   wherein the image processing unit can perform a plurality of types of gradation conversion on the image data, and performs a predetermined type of gradation conversion according to an output of the photographing mode selection unit.

7. The ophthalmologic photographing apparatus according to claim 6, wherein in a case where a color photographing mode is selected by the photographing mode selection unit, the image processing unit performs gradation conversion based on gradation information of the image data.

8. The ophthalmologic photographing apparatus according to claim 1, wherein the imaging unit and the image data generation unit are integrally configured as a digital camera, the digital camera being able to be detachably mounted on a fundus camera.

9. The ophthalmologic photographing apparatus according to claim 1, wherein, in a case where a red-free photographing mode is selected by the photographing mode selection unit, the image data generation unit generates an image data having the spatial resolution higher than that of the image data generated in a color photographing mode and the gradation resolution higher than that of an image data generated in the fluorescent photographing mode.

10. The ophthalmologic photographing apparatus according to claim 1, wherein the image data generation unit generates the image data having a larger number of bits per pixel as the higher gradation resolution and image data having a smaller number of pixels per screen as the lower spatial resolution from electric data of the captured image in a case where the color photographing mode is selected by the photographing mode selection unit than in a case where the fluorescent photographing mode is selected by the photographing mode selection unit.

11. A photographing apparatus for photographing a subject's eye in any of a plurality of photographing modes differing from one another in photographing condition, the photographing apparatus comprising a generation unit configured to generate, in a case where the subject's eye is photographed in a color photographing mode, image data by taking precedence of a gradation resolution over a spatial resolution from electric data of an image of the subject's eye photographed in the color photographing mode.

12. The photographing apparatus according to claim 11, wherein the generation unit generates the image data having a larger number of bits per pixel as the gradation resolution and image data having a smaller number of pixels per screen as the spatial resolution from electric data of an image of the subject's eye photographed in the color photographing mode than in a case where a fluorescent photographing mode is selected.

13. An ophthalmologic photographing system comprising:
a photographing unit configured to photograph a subject's eye in any of a plurality of photographing modes differing from one another in photographing condition, and
a generation unit configured to generate, in a case where the subject's eye is photographed in a color photographing mode, image data by taking precedence of a gradation resolution over a spatial resolution from the electric data of an image of the subject's eye photographed in the color photographing mode.

14. The ophthalmologic photographing system according to claim 13, wherein, in a case where the subject's eye is photographed in the color photographing mode, the generation unit performs processing to reduce spatial resolution of the electric data.

15. The ophthalmologic photographing system according to claim 13, wherein, in a case where the subject's eye is photographed in a fluorescent photographing mode, the generation unit generates the image data by taking precedence of the spatial resolution over the gradation resolution.

16. The ophthalmologic photographing system according to claim 13, wherein, in a case where the image of the subject's eye is photographed in a fluorescent photographing mode, the generation unit performs processing to reduce gradation resolution of electric data of an image of the subject's eye photographed in the fluorescent photographing mode.

17. The ophthalmologic photographing system according to claim 13, further comprising:
a data transfer unit configured to transfer the image data generated by the generation unit; and
an image processing unit configured to perform, according to the photographing mode in which the image of the subject's eye is photographed, a gradation conversion process of the image data transferred by the transfer unit.

18. The ophthalmologic photographing system according to claim 17, wherein, in a case where the image of the subject's eye is photographed in a fluorescent photographing mode, the image processing unit restores the transferred image data which is in compression and performs the gradation conversion process of the restored image data according to the fluorescent photographing mode.

19. The ophthalmologic photographing system according to claim 13, wherein the generation unit generates the image data having a larger number of bits per pixel as the gradation resolution and image data having a smaller number of pixels per screen as the spatial resolution from the electric data of an image of the subject's eye photographed in the color photographing mode than in a case where the fluorescent photographing mode is selected.

20. An ophthalmologic photographing apparatus comprising:
a photographing mode selection unit configured to select one of a plurality of photographing modes respectively corresponding to different photographing conditions;
an imaging unit configured to capture an image of a subject's eye;
an image data generation unit configured to generate an image data having spatial resolution higher than that of the plurality of image data generated in a color photographing mode from electric data of the captured image in a case where a red-free photographing mode is selected by the photographing mode selection unit.

21. The ophthalmologic photographing apparatus according to claim 20, wherein, in a case where a color photographing mode is selected by the photographing mode selection unit, the image data generation unit generates an image data by taking precedence of the gradation resolution over the spatial resolution.

22. The ophthalmologic photographing apparatus according to claim 20, wherein the image data generation unit generates the image data having the gradation resolution higher than that of the plurality of image data generated in a fluorescent photographing mode.

23. An ophthalmologic photographing method comprising:
capturing an image of a subject's eye in any of a plurality of photographing modes differing from one another in photographing condition;
generating an image data having a higher gradation resolution and a lower spatial resolution from electric data of the captured image in a case where a color photographing mode is selected than in a case where a fluorescent photographing mode is selected.

24. A non-transitory computer readable medium having program code thereon for causing an ophthalmologic apparatus to perform the ophthalmologic photographing method according to claim 23.

25. The ophthalmologic photographing method according to claim 23, wherein in the generating step, generating the image data having a larger number of bits per pixel as the higher gradation resolution and image data having a smaller number of pixels per screen as the lower spatial resolution from electric data of the captured image in a case where the color photographing mode is selected than in a case where the fluorescent photographing mode is selected.

26. An ophthalmologic photographing method comprising:
photographing a subject's eye in any of a plurality of photographing modes differing from one another in photographing condition, and generating, in a case where the subject's eye is photographed in a color photographing mode, image data by taking precedence of a gradation resolution over a spatial resolution from the electric data of an image of the subject's eye photographed in the color photographing mode.

27. A non-transitory computer readable medium having program code thereon for causing an ophthalmologic apparatus to perform the ophthalmologic photographing method according to claim 26.

28. The ophthalmologic photographing method according to claim 26, wherein in the generating step, generating the image data having a larger number of bits per pixel as the gradation resolution and image data having a smaller number of pixels per screen as the spatial resolution from the electric data of an image of the subject's eye photographed in the color photographing mode than in a case where the fluorescent photographing mode is selected.

29. A photographing apparatus for photographing a subject's eye in any of a plurality of photographing modes differing from one another in photographing condition, the photographing apparatus comprising a generation unit configured to generate an image data having a larger number of bits per pixel from electric data of a photographed image of the subject's eye in a case where a color photographing mode is selected than in a case where a fluorescent photographing mode is selected.

30. A photographing method comprising:
    photographing a subject's eye in any of a plurality of photographing modes differing from one another in photographing condition, and
    generating an image data having a larger number of bits per pixel from electric data of the captured image a photographed image of the subject's eye in a case where a color photographing mode is selected than in a case where a fluorescent photographing mode is selected.

31. A non-transitory computer readable medium having program code thereon for causing a photographing apparatus to perform the photographing method according to claim 30.

32. A photographing apparatus for photographing a subject's eye in any of a plurality of photographing modes differing from one another in photographing condition, the photographing apparatus comprising a generation unit configured to generate an image data having a smaller number of pixels per screen from electric data of a photographed image of the subject's eye in a case where a color photographing mode is selected than in a case where a fluorescent photographing mode is selected.

33. A photographing method comprising:
    photographing a subject's eye in any of a plurality of photographing modes differing from one another in photographing condition, and
    generating an image data having a smaller number of pixels per screen from electric data of a photographed image of the subject's eye in a case where a color photographing mode is selected than in a case where a fluorescent photographing mode is selected.

34. A non-transitory computer readable medium having program code thereon for causing a photographing apparatus to perform the photographing method according to claim 33.

* * * * *